(12) United States Patent
Hosaka et al.

(10) Patent No.: US 8,313,483 B2
(45) Date of Patent: Nov. 20, 2012

(54) MICROWAVE ENDOSCOPE FORCEPS

(75) Inventors: Makoto Hosaka, Ritto (JP); Tohru Tani, Otsu (JP); Yoshimasa Kurumi, Otsu (JP); Shigeyuki Naka, Otsu (JP)

(73) Assignee: National University Corporation Shiga University of Medical Science, Shiga (JP)

( * ) Notice: Subject to any disclaimer, the term of this patent is extended or adjusted under 35 U.S.C. 154(b) by 563 days.

(21) Appl. No.: 12/513,559

(22) PCT Filed: Nov. 8, 2007

(86) PCT No.: PCT/JP2007/071696
§ 371 (c)(1),
(2), (4) Date: Jun. 3, 2009

(87) PCT Pub. No.: WO2008/056732
PCT Pub. Date: May 15, 2008

(65) Prior Publication Data
US 2010/0023001 A1    Jan. 28, 2010

(30) Foreign Application Priority Data
Nov. 9, 2006  (JP) .................................. 2006-304589

(51) Int. Cl.
*A61B 18/18* (2006.01)
(52) U.S. Cl. ........... 606/33; 606/170; 606/207; 606/208
(58) Field of Classification Search .............. 606/50–52, 606/205–207
See application file for complete search history.

(56) References Cited

U.S. PATENT DOCUMENTS 5,423,854 A * 6/1995 Martin et al. .................. 606/205
6,682,548 B2 * 1/2004 Lang et al. .................... 606/205

FOREIGN PATENT DOCUMENTS

| JP | H01-232948 | 9/1989 |
| JP | H05-253241 | 5/1993 |
| JP | 2005-021658 | 1/2005 |
| JP | 2005-312807 | * 11/2005 |
| WO | WO 2004/108001 A1 | 12/2004 |

* cited by examiner

*Primary Examiner* — Linda Dvorak
*Assistant Examiner* — Jaymi Della
(74) *Attorney, Agent, or Firm* — Joseph Hyosuk Kim; JHK Law

(57) ABSTRACT

Provided is an operating tool for organism, in particular, a microwave endoscope forceps. In terms of the operating tool for organism, provided is a multifunctional operating tool which has holding and scissors functions simultaneously, and may further perform coagulation (tissue fixation) by microwaves. The operating tool has no definite fulcrum, and has both the holding and scissors functions with a simple structure by deforming a long-track rod called beam. Two blades are insulated from each other so as to allow microwave current supply. With this structure, an operating tool having three functions, i.e., "a holding function", "a coagulating function", and "a cutting function" with a single tool may be developed.

10 Claims, 5 Drawing Sheets

MICROWAVE ENDOSCOPE FORCEPS

TECHNICAL FIELD

The present invention relates to an operating tool for organism, and more particularly, to a microwave endoscope forceps.

BACKGROUND ART

Tools each having a different function are used in a surgical operation. However, each of the tools is equipped with a single function, and hence the tools need to be replaced for every working, thereby causing complicated workings. Further, in an operation by a robot, functional legs need to be replaced for each working, thereby bringing a cause of extension of an operation time. Accordingly, a multifunctional operating tool formed of a single tool is required. As one used in an operation under observation with an endoscope, there is disclosed a high frequency treatment apparatus (Patent Document 1) capable of holding, coagulating (stanching), separating tissues, and as one used in an operation using microwaves, there is disclosed a treatment instrument (Patent Document 2) capable of holding, coagulating, cutting tissues. However, there are limits of performing micro cutting under extra-fine specification of an endoscope, a catheter, or the like.
Patent Document 1: JP 5-253241 A
Patent Document 2: JP 2005-021658 A

DISCLOSURE OF THE INVENTION

Problem to be Solved by the Invention

In order to solve the above-mentioned problem, in terms of an operating tool for organism, it is an object of the present invention to provide a multifunctional operating tool which has holding and scissors functions simultaneously, and may further perform coagulation (tissue fixation) by microwaves.

Means for Solving the Problem

In general, for holding an article, it is necessary that two surfaces be parallel to each other. Meanwhile, the principle of scissors resides in that cutting is performed by crossing end surfaces of two surfaces. Thus, it is very difficult to obtain both holding and scissors functions simultaneously. Further, a general forceps has such a structure that a fulcrum exists and a cutting edge portion moves using the fulcrum as a center, and hence it is impossible to obtain both the holding function and the scissors function simultaneously, or if possible, a complex mechanism is necessary. The operating tool of the present invention has no definite fulcrum, and has both holding and scissors functions with a simple structure by deforming a long-track rod called beam. Further, two blades are insulated from each other so as to allow the supply of microwave current. With this structure, an operating tool having three functions, i.e., "a holding function", "a coagulating function", and "a cutting function" with a single tool may be developed.

The present invention includes the following.

1. An operating tool for organism having a holding function and a scissors function, the operating tool comprising a movable blade and a fixed blade serving as an upper blade and a lower blade, respectively,
the movable blade including:
a fulcrum portion, which is provided as a fulcrum at one end thereof obliquely opposite to a blade portion, and is connected to an elastic long-track rod; and
a portion (connecting portion) to be connected to an elastic drive carrier, the portion being provided downward of the fulcrum portion of the movable blade while opposing the fulcrum portion thereof,
the blade portion of the movable blade being vertically movable by pushing and pulling the elastic drive carrier,
the fixed blade has a surface which is flat with respect to the movable blade,
a top end of the movable blade having no cutting function, the operating tool for organism being configured such that:
the movable blade moves upward so as to secure a space by pushing the elastic drive carrier and moves downward by pulling the elastic drive carrier, whereby the operating tool for organism is capable of holding an object to be treated in such a state that the top end of the movable blade and a flat surface portion of the fixed blade are faced in parallel with each other, and
a cutting edge portion of the movable blade moves in a lateral-axis (Y-axis) direction by further pulling the elastic drive carrier owing to asymmetry of a force applied from the elastic drive carrier to the movable blade and obliquely upward deformation of the long-track rod, and the cutting edge portion of the movable blade falls down from the fixed blade, whereby the operating tool for organism has a function of cutting the object to be treated by edge portions of the movable blade and the fixed blade.

2. An operating tool for organism according to the above item 1, wherein:
the elastic drive carrier and the movable blade are movably connected to each other at the connecting portion;
a connection shaft is perpendicularly passed through the movable blade;
the elastic drive carrier has a straight portion and a curved portion with respect to the lateral-axis (Y-axis) direction;
when the straight portion of the elastic drive carrier is pushed out and pulled in through a guide portion, a force in the lateral-axis (Y-axis) direction does not act on the movable blade;
by pushing out and pulling in the straight portion of the elastic drive carrier through the guide portion, the long-track rod and the movable blade make rotational movement using the connecting portion as a fulcrum so as to move upward and downward the cutting edge portion of the movable blade;
from such a state that the movable blade and the fixed blade are parallel to each other, by further pulling in the elastic drive carrier, the long-track rod deflects, and a blade base portion of the movable blade is lifted up owing to the deflection;
when the curved portion of the elastic drive carrier then starts to enter the guide portion, a portion of the curved portion offset from a center line of the elastic drive carrier generates a force toward the center line so that the elastic drive carrier imparts the force in the lateral-axis (Y-axis) direction to the movable blade;
a point at which the force in the lateral-axis (Y-axis) direction is applied to the movable blade by the elastic drive carrier and a point at which a force is applied to the movable blade by a resistance force of the long-track rod are offset from each other so that the movable blade makes rotational movement about a vertical-axis (Z-axis); and
by this rotational movement under such a state that a blade base of the movable blade is lifted up, positional shift of the movable blade in the lateral-axis (Y-axis) direction becomes larger at the cutting edge portion than at the blade base portion so that the movable blade may fall down from its cutting edge portion to a side of the fixed blade, whereby the edge portions of the movable blade and the fixed blade have the function of cutting the object to be treated.

3. An operating tool for organism according to the above item 1 or 2, wherein the elastic drive carrier is formed into a wire-like shape.

4. An operating tool for organism according any one of the above items 1 to 3, wherein:

the long-track rod is a conductor for microwave transmission;

the fixed blade and the movable blade are insulated from each other; and microwaves are transmitted to the blade portion of the movable blade through electrification.

5. An operating tool for organism according to the above item 4, wherein:

the object to be treated is held under such a state that the movable blade and the fixed blade are parallel to each other;

coagulation treatment by the microwaves may be achieved through electrification; and the movable blade falls down from its cutting edge portion to the side of the fixed blade, if further desired, whereby the edge portions of the movable blade and the fixed blade cut the object to be treated.

6. An operating tool for organism according any one of the above items 1 to 5, wherein a material for the operating tool for organism is a non-magnetic material.

7. An operating tool for organism according any one of the above items 4 to 6, which is used for coagulating, stanching, and cutting duct tissues typified by blood vessels and bile ducts.

8. An operating tool for organism according any one of the above items 4 to 6, which is used for coagulating, stanching, and cutting cancerous tissues.

9. An operating tool for organism according any one of the above items 4 to 6, which is used for cutting a surgical suture.

10. An operating tool for organism according any one of the above items 1 to 9, wherein the conductor allows alternating-current transmission or direct-current transmission.

Effects of the Invention

The operating tool of the present invention is primary directed to operations under observation using an endoscope and a celoscope. However, by making a design change in a similar way, the operating tool may be used in general surgical operations, neurosurgery, and otolaryngology. The operating tool is manufactured from a non-magnetic metal material so as to allow microwave current supply, and may be used in an operation under observation with an MR microscope. The operating tool of the present invention is a multifunctional forceps in which "a holding function of gripping tissues" and "a scissors function of cutting tissues" are combined, and is used for coagulating, stanching, and cutting duct tissues such as blood vessels and bile ducts and for coagulating, stanching, and removing cancerous tissues. Further, the operating tool is applicable for cutting surgical appliances such as a surgical suture. In addition, a shaft may be made of a soft or hard material, and a blade may be a straight or curved blade. Such a design change may be made so as to be used under observation with an endoscope, a laparoscope, and eyes.

BRIEF DESCRIPTION OF THE DRAWINGS

FIGS. 4a and 4b each illustrate a state in which opposed surfaces of a movable blade (4) and a fixed blade (3) are parallel to each other, in which FIG. 4a is a top view, and FIG. 4b is a side view of a structure of a drive wire;

FIGS. 5c and 5d each illustrate a state in which a blade base portion of the movable blade (4) is lifted up, in which FIG. 5c is a top view, and FIG. 5d is a side view of the structure of the drive wire; and FIGS. 6e and 6f each illustrate a state in which the movable blade (4) falls from its cutting edge portion to a side of the fixed blade (3), in which FIG. 6e is a top view, and FIG. 6f is a side view of the structure of the drive wire.

Figure 1:
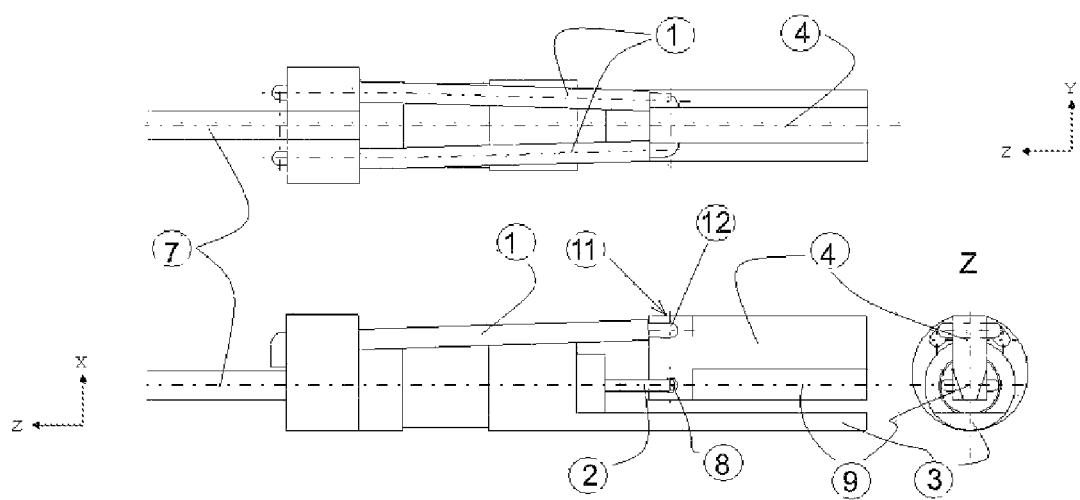
FIG. 1 are a top view (X), a side view (Y), and a front view (Z), respectively, of a medical treatment instrument of the present invention.

DESCRIPTION OF SYMBOLS 1 beam
2 drive wire
3 fixed blade
4 movable blade
5 TEFLON® (polytetrafluoroethylene) tube
6 polyimide tube
7 brass pipe
8 connecting point
9 blade portion
10 TEFLON® (polytetrafluoroethylene) tube
11 wiring groove
12 connecting point
13 guide portion
14 curved portion
15 straight portion of drive wire (2)

BEST MODE FOR CARRYING OUT THE INVENTION

Figure 2:
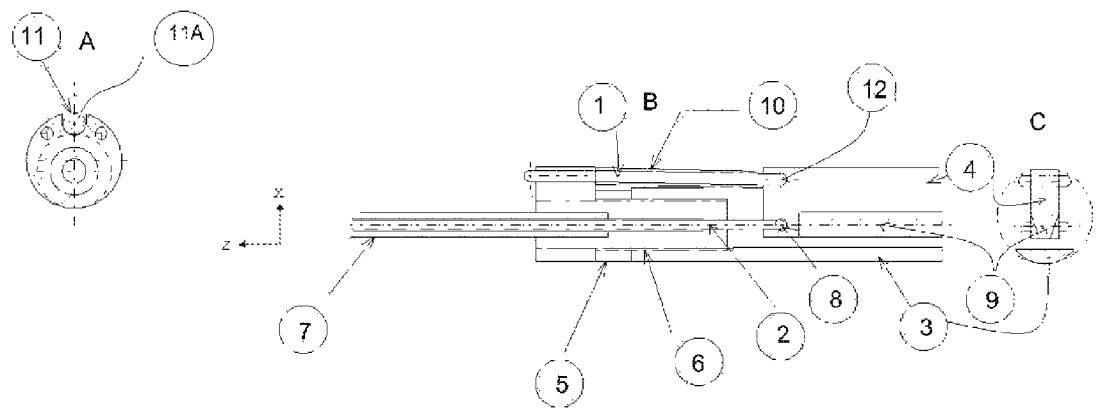
FIG. 2 are a rear view (A), a side view (B), and a front view (C), respectively, of an inner structure of the medical treatment instrument of the present invention.

In a structure of a medical treatment instrument of the present invention, a structure of a top end portion thereof mainly includes a movable blade, a fixed blade, a drive support called drive wire, and a long-diameter rod called beam, and the movable blade and the fixed blade are electrically insulated from each other. By pushing the drive wire, the movable blade is moved upward so as to secure an open space, and by pulling the drive wire weakly, the space is closed. By pulling the drive wire strongly, an object which has been held is cut. Owing to asymmetry of a force imparted from the drive wire to the movable blade and deflection of the beam, the movable blade is shifted to the side, and falls down from the fixed blade to cut the object which has been held. A cutting edge portion of the movable blade may be somewhat sharp, and does not need to be sharp enough to damage tissues by gripping the same. FIGS. 1 and 2 each illustrate the structure of the medical treatment instrument.

FIG. 1 are a top view (X), a side view (Y), and a front view (Z), respectively, of the medical treatment instrument of the present invention. In the top view (X), a beam (1) and a movable blade (4) are provided, and the movable blade (4) is supported by the beam (1). The side view (Y) illustrates the state in which the movable blade (4) as an upper blade and a fixed blade (3) as a lower blade are parallel to each other, and the movable blade (4) and the fixed blade (3) fall into place. The movable blade (4) has a blade portion (9), and the top end of the blade portion (9) is not sharp, and may hold an object to be treated by pinching the object to be treated together with the fixed blade (3). The beam (1) and the movable blade (4) are connected to each other at a connecting point (12) located on the front side of the upper end portion of the movable blade (4), and the connecting point (12) may function as a fulcrum. At the lower end portion of the movable blade (4) facing the connecting point (12), there is provided a connecting point (8) for connecting a drive wire (2) and the movable blade (4) to each other. The connecting point (8) may also function as a fulcrum. In the front view (Z), a shape of the medical treatment instrument viewed from front may be confirmed. It is illustrated that the top end of the blade portion (9) of the movable blade (4), which faces the fixed blade (3) having a flat surface directed upward, is flat and not sharp.

FIG. 2 are a rear view (A), a side view (B), and a front view (C), respectively, of an inner structure of the medical treatment instrument of the present invention. In the rear view (A), a wiring groove (11) and a coaxial central conductive wire with a film are illustrated, the coaxial central conductive wire being passed through the wiring groove (11). In the side view (B), a brass pipe (7), teflon (registered trade mark) tubes (5) and (10), a polyimide tube (6), the beam (1), the drive wire (2), the movable blade (4), the blade portion (9), and the fixed blade (3) are illustrated. In the front view (C), the movable blade (4), the blade portion (9), and the fixed blade (3) are mainly illustrated.

Figure 3:
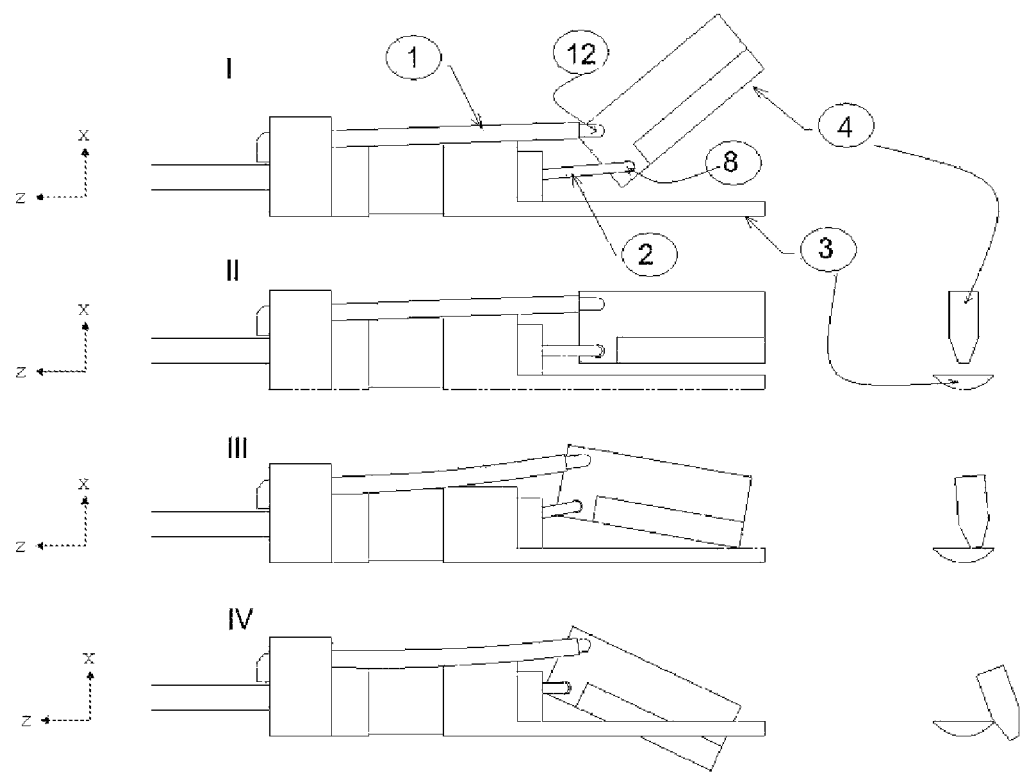
FIG. 3 illustrate operations of the medical treatment instrument of the present invention.

FIG. 3 each illustrate operations of the medical treatment instrument of the present invention. An opening state (I), a parallel state (II), a pinching state (III), and a cutting state (IV) are illustrated. In the opening state (I), by pushing out the drive wire (2), the top end of the movable blade (4) is lifted up with the fulcrum (12) being used as a center, and the movable blade (4) is moved upward so as to secure an open space. This operation leads to gripping of tissues or the like to be treated. In the parallel state (II), by pulling the drive wire (2) slightly, the movable blade (4) and the fixed blade (3) become parallel to each other so as to grip the tissues or the like to be treated, current is supplied between the movable blade (4) and the fixed blade (3), and, for example, microwaves are caused to flow therebetween, thereby coagulating the gripped tissues or the like. In the pinching state (III), the drive wire (2) is further pulled, and the cutting edge portion (9) of the movable blade (4) may be moved to the side (a state in which a contact surface of the movable blade and the fixed blade illustrated in the right-hand side of FIG. 3III is shifted slightly to the right side) by utilizing deformation of the beam (1) and asymmetry from the drive wire (2) to the movable blade (4), which is attributed to a shape of the drive wire (2). In the cutting state (IV), the drive wire (2) is still further pulled, and the cutting edge portion of the movable blade (4) falls down from the fixed blade (3), whereby cutting is performed on the gripped tissues or the like due to the contact between edge portions of the movable blade (4) and the fixed blade (3).

Figure 4:
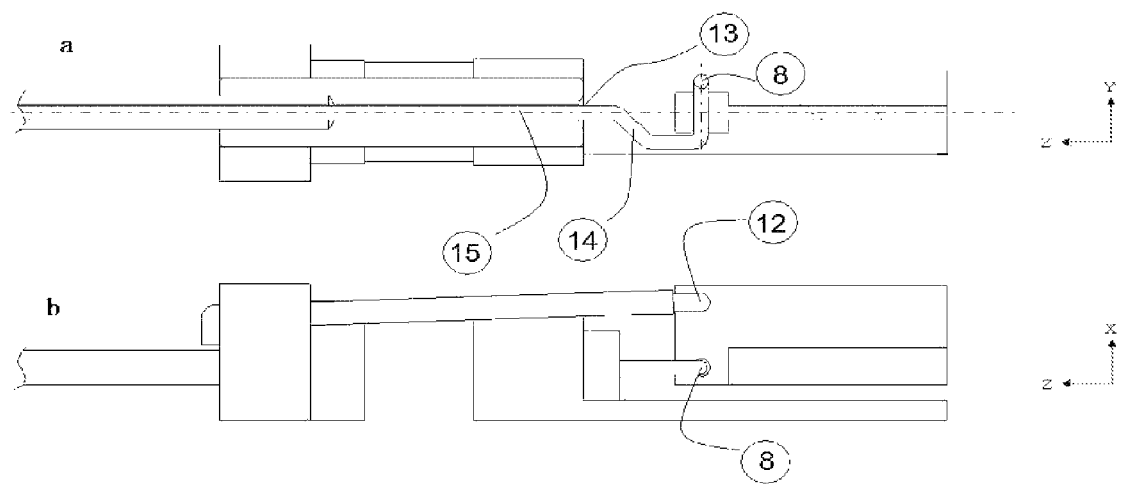
Figure 5:
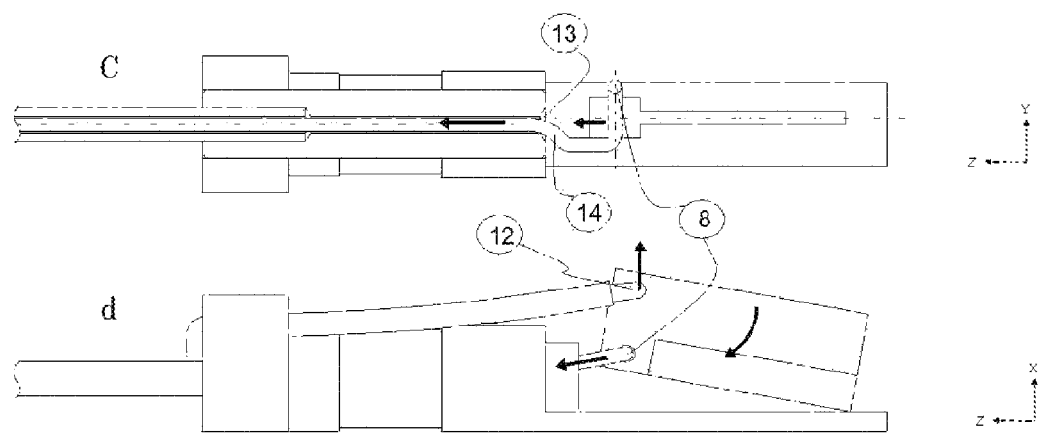
Figure 6:
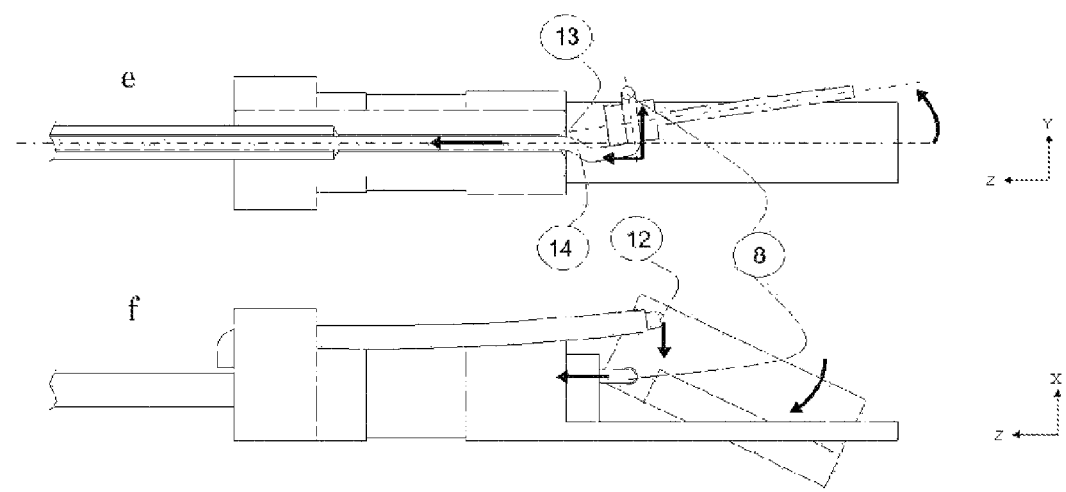

FIGS. 4 to 6 each illustrate a structure of the drive wire enabling to perform cutting by the above-mentioned gripping. The drive wire (2) serving as a drive support and the movable blade (4) are movably connected to each other at the connecting point (8), and a connection shaft is perpendicularly passed through the movable blade. The drive wire (2) has a straight portion and a curved portion with respect to a lateral-axis (Y-axis) direction. When a straight portion (15) of the drive wire (2) is pushed out and pulled in through a guide portion (13), a force in the lateral-axis (Y-axis) direction does not act on the movable blade (4). The straight portion (15) of the drive wire (2) is pushed out and pulled in through the guide portion (13), whereby the beam (1) serving as a long-track rod and the movable blade (4) make rotational movement using the connecting point (12) as a fulcrum so as to move upward and downward the cutting edge portion of the movable blade (4).

FIG. 4 each illustrate a state in which opposed surfaces of the movable blade (4) and the fixed blade (3) are parallel to each other.

FIG. 4a illustrates a structure of the drive wire viewed from above, and FIG. 4b is a side view thereof.

Under the state in which the movable blade (4) and the fixed blade (3) are parallel to each other, by further pulling in the drive wire (2), the beam (1) deflects, and the blade base portion of the movable blade (4) is lifted up owing to the deflection (FIG. 5). FIG. 5c illustrates the structure of the drive wire viewed from above, and FIG. 5d is a side view thereof. Then, when a curved portion (14) of the drive wire (2) starts to enter the guide portion (13), a portion of the curved portion (14) offset from a center line of the drive wire (2) generates a force toward the center line, whereby the drive wire (2) imparts the force in the lateral-axis (Y-axis) direction to the movable blade (4). A point at which the force in the lateral-axis (Y-axis) direction is applied to the movable blade (4) by the drive wire (2) and a point at which a force is applied to the movable blade (4) by a resistance force of the beam (1) are offset from each other, and hence the movable blade (4) makes rotational movement about a vertical-axis (Z-axis). By this rotational operation under the state in which the blade base of the movable blade (4) is lifted up, positional shift of the movable blade (4) in the lateral-axis (Y-axis) direction becomes larger at the cutting edge portion than at the blade base portion, and hence the movable blade (4) may fall down from its cutting edge portion to the side of the fixed blade (3) (FIG. 6). FIG. 6e illustrates the structure of the drive wire viewed from above, and FIG. 6f is a side view thereof. As a result, edge portions of the movable blade (4) and the fixed blade (3) cut tissues or the like to be treated.

FIG. 2 are a rear view (A), a side view (B), and a front view (C), respectively, of an inner structure of the medical treatment instrument of the present invention. In the rear view (A), a wiring groove (11) and a coaxial central conductive wire with a film (11a) are illustrated, the coaxial central conductive wire being passed through the wiring groove (11). In the side view (B), a brass pipe (7), TEFLON® (polytetrafluoroethylene) tubes (5) and (10), a polyimide tube (6), the beam (1), the drive wire (2), the movable blade (4), the blade portion (9), and the fixed blade (3) are illustrated. In the front view (C), the movable blade (4), the blade portion (9), and the fixed blade (3) are mainly illustrated.

INDUSTRIAL APPLICABILITY

According to the present invention, there is provided a medical treatment instrument capable of achieving holding, compressing, stanching, coagulating, and cutting of biotissues by one operation in medical surgical treatment, of easy manipulation, and of separation. According to the medical treatment instrument of the present invention, there is provided a multifunctional medical treatment instrument capable of holding, coagulating (stanching), and cutting of biotissues with use of a power source capable of supplying the microwaves even under observation of an inside of the biotissues using a mirror, an endoscope, a catheter, or the like. The medical treatment instrument of the present invention may be used for coagulating, stanching, and cutting of duct tissues typified by bile ducts and blood vessels, and in particular for coagulating, stanching, and cutting cancerous tissues. In addition, the medical treatment instrument of the present invention may be used for cutting a surgical suture.

The invention claimed is:

1. An operating tool for an organism having a holding function and a scissors function, the operating tool comprising a movable blade and a fixed blade serving as an upper blade and a lower blade, respectively, and wherein said operating tool is characterized by:
the movable blade comprising:
a first connecting portion, which is provided as a fulcrum at one end thereof obliquely opposite to a blade portion; and
a second connecting portion to be connected to an elastic drive carrier, the second connecting portion being provided opposing the first connecting portion,
a top end of the movable blade having no cutting function,
the first connecting portion being connected to an elastic beam,
the fixed blade having a flat surface with respect to the movable blade,
the drive carrier having a straight portion and a curved portion,
the operating tool for organism being configured such that:
when the straight portion of the drive carrier is pushed out and pulled in through a guide portion, the blade portion of the movable blade is capable of moving orthogonally with respect to a plane of the flat surface of the fixed blade, hinging upon the first connecting portion as a fulcrum,
whereby the operating tool for an organism is capable of holding an object to be treated in such a state that the top end of the movable blade is capable of moving orthogonally with respect to the plane of the flat surface of the fixed blade, hinging upon the first connecting portion as a fulcrum and a portion of the flat surface of the fixed blade are faced in parallel with each other; and
when the curved portion of the drive carrier then starts to enter the guide portion, a portion of the curved portion offset from a center line of the drive carrier generates a force toward the center line so that the drive carrier imparts the force to the movable blade such that the movable blade makes rotational movement about an axis along the straight portion of the drive carrier, and, by this rotational movement, the movable blade falls down to a side of the fixed blade, whereby the movable blade and the fixed blade are capable of cutting the object to be treated.

2. An operating tool for an organism having the holding function and the scissors function according to claim 1, wherein:
from such a state that the movable blade and the fixed blade are parallel to each other, by further pulling in the drive carrier through the guide portion, the elastic beam deflects, and a blade base portion of the movable blade is lifted up owing to the deflection; and
under a state in which the blade base portion is lifted up, when the curved portion of the drive carrier then starts to enter the guide portion, the portion of the curved portion offset from the center line of the drive carrier generates the force toward the center line so that the drive carrier imparts the force to the movable blade such that the movable blade makes rotational movement about the axis along the straight portion of the drive carrier, and, by this rotational movement, the movable blade falls down from the cutting edge portion to the side of the fixed blade, whereby the movable blade comes into contact with the object to be treated from the cutting edge portion to the blade base portion, to thereby be capable of cutting the object to be treated.

3. An operating tool for an organism according to claim 1, wherein the elastic drive carrier is formed into a wire-like shape.

4. An operating tool for an organism according to claim 1, wherein:
the fixed blade and the movable blade are insulated from each other; and
microwaves are transmitted to the blade portion of the movable blade through electrification.

5. An operating tool for an organism according to claim 4, wherein:
the object to be treated is held under such a state that the movable blade and the fixed blade are parallel to each other;
coagulation treatment by the microwaves may be achieved through electrification; and
the movable blade falls down from its cutting edge portion to the side of the fixed blade, if further desired, whereby the edge portions of the movable blade and the fixed blade cut the object to be treated.

6. An operating tool for an organism to claim 1, wherein a material for the operating tool for organism is a non-magnetic material.

7. An operating tool for an organism according to claim 1, which is used for coagulating, stanching, and cutting duct tissues typified by blood vessels and bile ducts.

8. An operating tool for an organism according to claim 1, which is used for coagulating, stanching, and cutting cancerous tissues.

9. An operating tool for an organism according to claim 1, which is used for cutting a surgical suture.

10. An operating tool for an organism according to claim 1, wherein the conductor allows alternating-current transmission or direct-current transmission.

* * * * *